United States Patent [19]
Bonnichsen et al.

[11] Patent Number: 5,984,906
[45] Date of Patent: Nov. 16, 1999

[54] SYRINGE SYSTEM

[75] Inventors: Frits Frydendal Bonnichsen, Lynge; Peter Nissen Jørgensen, Broenshoej, both of Denmark

[73] Assignee: Novo Nordisk A/S, Bagsvaerd, Denmark

[21] Appl. No.: 08/794,026

[22] Filed: Feb. 3, 1997

Related U.S. Application Data

[63] Continuation of application No. 08/550,494, Oct. 30, 1995, Pat. No. 5,599,323, which is a continuation of application No. 08/323,401, Oct. 14, 1994, Pat. No. 5,462,535, which is a continuation-in-part of application No. 08/167,831, Dec. 16, 1993, abandoned, which is a continuation of application No. PCT/DK92/00212, Jul. 2, 1992.

[30] Foreign Application Priority Data

Jul. 12, 1991 [DK] Denmark ................ 1346/91

[51] Int. Cl.⁶ ..................... A61M 5/32
[52] U.S. Cl. ............ 604/272; 604/232; 604/239
[58] Field of Search .............. 604/272, 239, 604/232, 273, 274, 51, 52

[56] References Cited

U.S. PATENT DOCUMENTS

| | | |
|---|---|---|
| 4,313,439 | 2/1982 | Babb et al. . |
| 4,413,760 | 11/1983 | Paton . |
| 4,552,561 | 11/1985 | Eckenhoff et al. . |
| 4,592,745 | 6/1986 | Rex et al. . |
| 4,745,068 | 5/1988 | Godfrey et al. . |
| 4,865,591 | 9/1989 | Sams . |
| 4,883,472 | 11/1989 | Michel . |
| 4,894,054 | 1/1990 | Miskinyar . |
| 4,936,833 | 6/1990 | Sams . |
| 4,973,318 | 11/1990 | Holm et al. . |
| 4,976,701 | 12/1990 | Ejlersen et al. . |
| 5,017,190 | 5/1991 | Simon et al. . |
| 5,042,977 | 8/1991 | Bechtold et al. . |
| 5,092,842 | 3/1992 | Bechtold et al. . |
| 5,104,380 | 4/1992 | Holman et al. . |
| 5,112,317 | 5/1992 | Michel . |
| 5,114,406 | 5/1992 | Gabriel et al. . |
| 5,226,896 | 7/1993 | Harris . |
| 5,232,459 | 8/1993 | Hjertman . |
| 5,295,976 | 3/1994 | Harris . |
| 5,304,152 | 4/1994 | Sams . |
| 5,308,340 | 5/1994 | Harris . |
| 5,462,535 | 10/1995 | Bonnichsen et al. ............ 604/272 |
| 5,626,566 | 5/1997 | Petersen et al. . |

FOREIGN PATENT DOCUMENTS

| | | |
|---|---|---|
| 0 279 583 A2 | 8/1988 | European Pat. Off. . |
| WO 93/07922 | 4/1993 | WIPO . |

OTHER PUBLICATIONS

"Hypodermic, Disposable Needles: Mechanical Properties and Pain Perception as Function of Needle Diameter", by Lene Lytzen, Jun. 1991.

"How to Avoid Clogging of Insulin Syringes", *Diabetes Forecast* 1976.

"A Single–Blind, Randomized Study On The Degree Of Pain And Bleedings Using 27, 28 and 30 Gauge Needles", Sørensen et al. 9th Workshop of the Aidspit Study Group, Jan. 28–30, 1990.

Poster entitled, "Determination of Pain on Needle Penetration Using 27, 28 and 30 Gauge Insuject Needles", Sørensen et al., 9th Workshop of the Aidspit Study Group, Jan. 1990, p. 11, MedView 1987, vol. 1, No. 5.

"Submission of Becton Dickinson's Exhibits 46–49" in *Novo Nordisk A/S v. Becton–Dickinson & Co.*, 96 Civ. 9506 (S.D.N.Y.).

Nielsen Report on U.S. Sales of Disposable Insulin Syringes 1988–1991.

*Primary Examiner*—John D. Yasko
*Attorney, Agent, or Firm*—Steven T. Zelson, Esq.

[57] ABSTRACT

An insulin injection system comprises a pen shaped syringe with a cartridge containing insulin, and an injection needle. The needle is a G30 needle and the insulin is a type which may freely flow through a G 30 needle. When the insulin is the type comprising suspended crystals the maximal dimension of any crystal is 15 μm.

14 Claims, 2 Drawing Sheets

SYRINGE SYSTEM

CROSS-REFERENCE TO RELATED APPLICATIONS

This application is a continuation application of application Ser. No. 08/550,494, now U.S. Pat. No. 5,599,323, which was filed on Oct. 30, 1995, which is a continuation of application Ser. No. 08/323,401 filed on Oct. 14, 1994, now U.S. Pat. No. 5,462,535, which is a continuation-in-part of copending U.S. Ser. No. 08/167,831 filed Dec. 16, 1993, now abandoned, which is a continuation of PCT/DK92/00212 filed Jul. 2, 1992, the contents of which are incorporated herein by reference in their entirety.

BACKGROUND OF THE INVENTION

The invention relates to syringes for injecting insulin and more specified pen-shaped syringes administering insulin doses from a cartridge in the pen syringe.

Diabetes is usually treated by the patient frequently injecting himself with an insulin dose which he adjusts each time according to his immediate need.

To make it less straining to the patient to prick himself several times a day, it is aspired to make the injections as painless as possible and to reduce the physical malaise many people will feel if they have to pass a needle into their own body.

As the malaise seems to grow with the length and the thickness of the needle and the sensation of pain seems to be reduced when the needle is made thinner, a passable way seems to be to make the needle thinner and shorter. This line may, of course, only be followed to a certain extent, as the needle must have a length permitting the subcutaneous injection of the insulin and a thickness allowing the insulin to pass through the needle.

Whereas the acceptable minimum length of the needle is well defined, the lower limit for the thickness of the needle is more fluid. With a thinner needle it becomes more difficult to press the insulin out through the needle and the injections will take more time. A more relevant lower limit is set by the fact that by injecting insulin types appearing as suspended crystals, a sieving of the suspension may occur, and the suspension injected may consequently have a lower concentration than expected.

The thickness of needles are indicated by a "G" and a gauge number increasing with thinner needles. Thus, the outer diameter of a G 27 needle is 0.4 mm, of a G 28 needle 0.36 mm, and of a G 30 needle 0.3 mm. The wall thickness of the needles is typically 0.075 mm, so that a G 27 needle has bore of 0.25 mm, whereas the bore of a G 30 needle is 0.15 mm.

Commonly, G 27 needles are used. However, according to Diabetes Forecast 1976; 29 page 27 problems are observed when G 27 needles and even thicker needles are used for injecting an insulin containing suspended crystals. The problem is a clogging of the needle during injection, which clogging is due to the fact that crystals of e.g. Lente insulin having a size of 20–40 µm have a tendency to align themselves across the inside of the needle. This clogging is observed during injection, especially if this injection is carried out too slowly. It must be presumed that a similar clogging occurs during the filling of the syringe thus making the filling impossible or at least having the effect that some of the crystals are retained with the consequence that the suspension sucked into the syringe has a lower concentration then expected.

Whereas the trend goes towards the use of G 28 needles this is seen as close to the limit of what is possible. G 29 needles are seen as needles for disposable syringes for insulin, but G 30 needles have so far been deemed unusable for injection of an insulin suspension.

SUMMARY OF THE INVENTION

The present invention is based on the surprising recognition that needles thinner than G 29 may be used for injecting insulin.

The present invention is, thus, related to an insulin injection system comprising a pen shaped syringe having a cartridge with insulin and an injection needle, the system being characterized in that the needle is a G 30 needle and the cartridge contains an insulin type which may flow freely through a G 30 needle.

DETAILED DESCRIPTION OF TEE INVENTION

By the use of a pen shaped syringe with a cartridge the insulin will only have to pass the needle once, which in itself halves the risk of sieving. Further, the use of suspensions of insulin types having very short and needle shaped crystals totally eliminates the risk of bridging in a G 30 needle when no dimension of the insulin crystals exceeds 15 µm.

By closely binding a G 30 needle to a system further comprising a pen-shaped syringe, it may be ensured that a pen syringe equipped with a G 30 needle will always contain insulin of a type which may pass through the needle without any sieving effect.

The pen syringe may either be manufactured as a disposable device which is sold prefilled with the insulin or it may appear as a durable pen syringe so designed that it can only receive cartridges with insulin which may pass freely through a G 30 needle.

The needle may have attaching means cooperating with attaching means on the pen syringe for mounting the needle on the pen syringe, whereby the needle hub may be designed to only match with pen syringes of the system. Such attaching means may be a needle hub having a thread cooperating with a corresponding thread on the syringe.

The needle hub may have a central protrusion covering part of the length of the needle. Thereby, the length of the injection part of the needle is made shorter, which is advantageous as well from a psychological point of view as from a mechanical one. The protrusion makes visible only the part which should be inserted and it supports the thin and consequently more fragile needle.

With an injection part of the needle of 8–12 mm, it is avoided that the injections become intermuscular instead of subcutaneous. The needles may be manufactured in the same length as usual for thicker needles and the shorter injection part may be obtained by the hub protrusion covering a larger part than usual for the needle.

Figure 1:
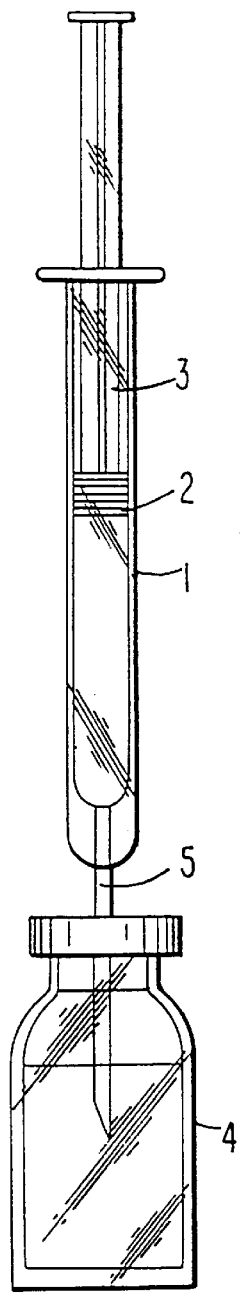
FIG. 1 shows an injection system comprising a disposable syringe and a vial.

FIG. 1 shows a disposable syringe comprising a tube 1 wherein a piston 2 may be displaced by pulling or pressing a piston rod 3. The syringe has an injection needle 5 integral with the tube 1. A vial 4 closed by a not shown rubber membrane contains insulin which may be sucked up into the syringe tube by piercing the membrane by the needle to immerse this needle into the insulin solution or suspension in the vial and thereafter pulling the piston rod to move the piston in the tube to establish a subatmospheric pressure beneath that piston.

The injection needle may be of the G 30 type, but nothing guarantees that the content in the vial may be sucked through such a needle without any sieving effect occurs. Or in other words, it is not ensured that the crystals of a suspension in the vial are small enough to pass a G 30 needle without difficulties.

Figure 2:
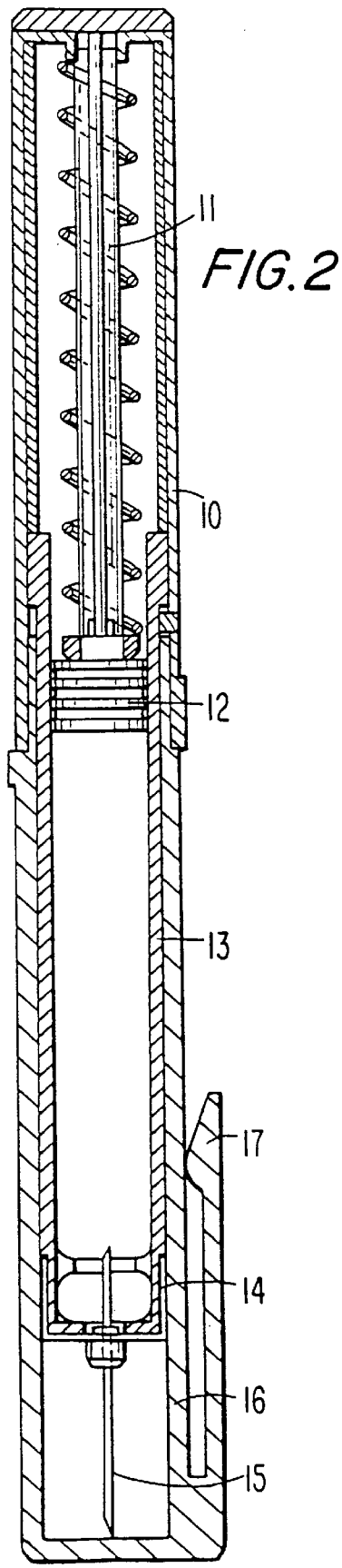
FIG. 2 shows an injection system according to the invention comprising a disposable pen syringe with an integrated cartridge and a needle hub with a needle.

FIG. 2 shows an injection system comprising a pen shaped syringe comprising a housing 10 containing a dosing mechanism which enables the user to set a dose which is by a piston rod 11 and a piston 12 pressed from a cartridge 13 integrated in the pen out through an injection needle 15 which is carried in a needle hub 14 screwed onto the distal end of the integrated cartridge so that a proximal end of the needle pierces a rubber membrane closing the distal end of the cartridge. The pen may be used for injection of several doses. When not in use, the needle is protected by a cap 16 which further has a clip 17 making the pen storable in a pocket like a pencil. When the cartridge is empty, that is when the piston has been pressed all the way to the distal end of the cartridge, the whole unit with dosing mechanism and cartridge may be disposed of.

In this injection system it is ensured that the needle is only used with the integrated cartridge on which distal end it may be screwed, i.e. by filling the cartridge with an insulin type which has small crystals having an maximal size of 15 $\mu$m, this system ensures that G30 needle may be used without any risk of sieving effect on the insulin suspension when it is injected through such a needle.

Figure 3:
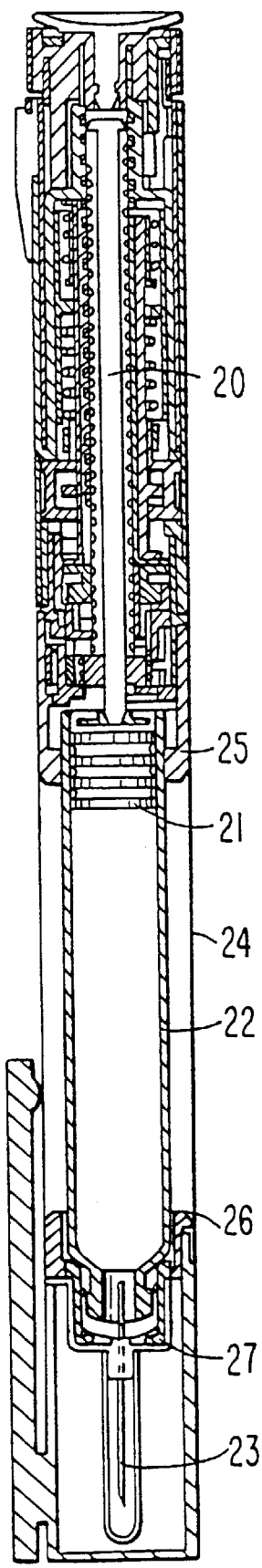
FIG. 3 shows an injection system according, to the invention comprising a reusable syringe loaded with a cartridge and carrying a needle hub with a needle.

In the system shown in FIG. 3 the pen syringe is of a reusable type in which a cartridge 22 is changed when empty. The pen syringe comprises a dosing part by which a piston rod 20 may successively be advanced to press a piston 21 into the cartridge 22 to press out corresponding doses of insulin through a needle 23 mounted at the distal end of the cartridge 22. The cartridge 22 is mounted in a cartridge holder comprising a tubular part 24 having at its proximal and distal ends guides 25 and 26, respectively, keeping the cartridge in a centered position in the holder.

The guide 26 at the distal end of the holder is so designed that a plastic cap 27 mounted on the neck part of the cartridge may protrude from the distal end of the syringe. The cap 27 carries an outer thread onto which may be mounted a needle hub with a G30 needle. In this way it is ensured that a G30 needle may only be mounted on a cartridge carrying a cap adapted to such a needle. When such caps are only mounted on cartridges filled with an insulin suspension having a crystal size <15 $\mu$m, i.e. an insulin type which may freely flow through a G30 needle, a safe injection system is provided.

Alternatively, the distal end of the cartridge holder may have a stud with an outer thread onto which a needle hub may be screwed. The injection system may then be made safe by taking care that the syringe can only be loaded with cartridges containing insulin suspensions wherein the crystal size is <15 $\mu$m.

Figure 4:
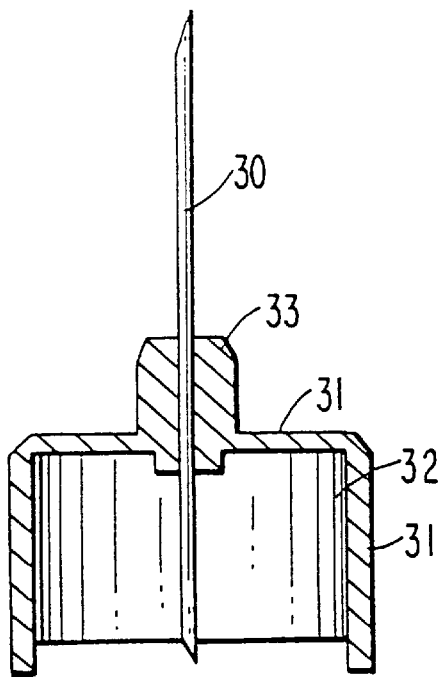
FIG. 4 shows a needle hub with a needle according to the invention.

FIG. 4 shows a needle hub with an embedded needle 30. The hub comprises a bottom 31 carrying a sleeve 31 which surrounds the needle concentrically at some distance. The sleeve has an internal thread 32 by which it may be screwed onto a hub receiving part of a syringe. A central protrusion 33 on the bottom 31 needle extends longitudinally along part of the needle 30 and forms a part of the embedment to let the needle be free only along the part of it which has to be inserted into the user during injection. In this way the risk of bending for breaking the needle is minimized.

We claim:

1. An insulin injection system comprising a pen shaped syringe comprising a cartridge with insulin and an injection needle, wherein the needle is thinner than a G-29 needle and the cartridge contains an insulin type which may freely flow through a needle thinner than a G-29 needle.

2. An insulin injection system according the claim 1, wherein the insulin type in the cartridge has a maximal crystals size of 15 $\mu$m.

3. An insulin injection system according to claim 1, wherein the pen shaped syringe is a disposable device prefilled with insulin.

4. An insulin injection system according to claim 1, wherein the pen shaped syringe is a durable device designed to receive only cartridges containing insulin which may pass freely through a thinner than G-29 needle.

5. An insulin injection system according to claim 1, wherein the needle has attaching means for cooperation with attaching means on the pen shaped syringe.

6. An insulin injection system according to claim 5, wherein the needle attaching means is a needle hub having a thread cooperating with a corresponding thread on the pen shaped syringe.

7. An insulin injection system according to claim 6, wherein the needle hub has a central protrusion covering part of the length of the needle.

8. An insulin injection system according to claim 7, wherein the length of the injection part of the needle is 8–12 mm.

9. An insulin injection system according to claim 2, wherein the pen shaped syringe is a disposable device prefilled with insulin.

10. An insulin injection system according to claim 2, wherein the pen shaped syringe is a durable device designed to receive only cartridges containing insulin which may pass freely through a thinner than G-29 needle.

11. A needle assembly comprising:
    (a) a needle hub having a base and a standard insulin needle fitting for removably mounting said needle assembly on a pen-type insulin syringe having a standard mounting and which accepts cartridges containing only insulin types that may flow freely through a thinner than G-29 needle; and
    (b) a thinner than G-29 needle secured in said base and having first and second needle portions extending from said base in opposite directions.

12. A needle assembly according to claim 11, wherein said standard fitting includes an annular sleeve extending from said base such that said sleeve surrounds said first needle portion concentrically and is spaced therefrom, and wherein said sleeve has a threaded interior by which it may be screwed onto a standard, externally threaded, hub-receiving part of a pen-type insulin syringe.

13. A needle assembly according to claim 12, and wherein said second needle portion has a predetermined length appropriate for injecting insulin into a human patient.

14. A needle assembly according to claim 13, wherein said base further comprises a central protrusion which extends from said base for a predetermined distance along said second needle portion and embeds said second needle portion along the said distance, and wherein said second needle portion further comprises an exposed end which projects axially from said central protrusion and which has a length corresponding to the desired depth of needle insertion into a human patient.

* * * * *